(12) United States Patent
Mathur

(10) Patent No.: US 6,416,540 B1
(45) Date of Patent: Jul. 9, 2002

(54) MAGNETICALLY ACTUATED CLEANABLE STENT AND METHOD

(76) Inventor: Sandip V. Mathur, 49 Glen Abbey, Abilene, TX (US) 79606

( * ) Notice: Subject to any disclaimer, the term of this patent is extended or adjusted under 35 U.S.C. 154(b) by 33 days.

(21) Appl. No.: 09/704,088

(22) Filed: Nov. 1, 2000

(51) Int. Cl.[7] .................................................. A61F 2/06
(52) U.S. Cl. ..................................................... 623/1.15
(58) Field of Search ............................. 623/1.15, 1.32, 623/1.1; 606/159, 198, 108, 151, 7, 48

(56) References Cited

U.S. PATENT DOCUMENTS

| | | |
|---|---|---|
| 3,674,014 A | 7/1972 | Tillander |
| 3,847,187 A | 11/1974 | Caillouette et al. |
| 4,698,058 A | 10/1987 | Greenfeld et al. |
| 4,733,665 A | 3/1988 | Palmaz |
| 5,195,984 A | 3/1993 | Schatz |
| 5,271,735 A | 12/1993 | Greenfeld et al. |
| B1 4,733,665 A | 1/1994 | Palmaz |
| 5,344,395 A | 9/1994 | Whalen et al. |
| 5,653,727 A | 8/1997 | Wiktor |
| 5,706,827 A | 1/1998 | Ehr et al. |
| 5,728,062 A | 3/1998 | Brisken |
| 5,846,218 A | 12/1998 | Brisken et al. |
| 5,851,185 A * | 12/1998 | Berns .......................... 600/434 |
| 5,928,261 A * | 7/1999 | Ruiz ........................... 606/159 |
| 5,931,805 A | 8/1999 | Brisken |
| 5,951,566 A * | 9/1999 | Lev ............................. 606/108 |
| 6,014,580 A | 1/2000 | Blume et al. |
| 6,015,414 A | 1/2000 | Werp et al. |
| 6,066,088 A * | 5/2000 | Davis .......................... 600/79 |
| 6,168,209 B1 * | 1/2001 | Cope et al. ................. 285/330 |
| 6,258,098 B1 * | 7/2001 | Taylor et al. ............... 606/108 |
| 6,319,242 B1 * | 11/2001 | Patterson et al. ........... 604/508 |

* cited by examiner

*Primary Examiner*—Michael J. Milano
*Assistant Examiner*—Tan-Uyen T. Ho
(74) *Attorney, Agent, or Firm*—Akin, Gump, Strauss, Hauer & Feld, LLP

(57) ABSTRACT

A tubular stent for placement within a vessel of a living being includes one or more elongated wire-like members lying adjacent the inner wall of the tubular body of the stent and responsive to magnetic forces acting thereon to thrash about within the lumen formed by the stent body to dislodge accumulated sediments and/or fatty deposits. The wire member or members may be configured to lie adjacent the inner wall of the stent body except when excited by an apparatus comprising plural pairs of electromagnets which may be energized sequentially to generate a moving force field acting on the stent.

20 Claims, 2 Drawing Sheets

MAGNETICALLY ACTUATED CLEANABLE STENT AND METHOD

FIELD OF THE INVENTION

The present invention pertains to a stent for providing support to a vessel lumen of a living being and which includes a member normally lying against the stent inner wall but which is responsive to magnetic forces to thrash about within the lumen of the stent to maintain the lumen free of debris accumulation.

BACKGROUND

A variety of medical conditions in living beings requires the use of a device to expand and/or support a constricted vessel and to maintain an open passageway or lumen through the vessel. Examples of such conditions include holding a dissection in place, preventing closure during spasm and preventing acute vessel closure during or due to thrombosis.

Stents used to permit the flow of fluids in blocked vessels or ducts, such as arteries that are blocked by fatty deposits, may be made of plastic or metal materials. Stents may be maneuvered into narrowed areas of the biliary system of the liver to permit drainage of bile. Stents may also provide palliation by opening a channel in a duct or vessel. Accordingly, stents may replace or delay the need for surgical procedures to open or maintain a suitable passageway or lumen in a duct or vessel.

A major drawback of stents is the tendency for the passageway or lumen of the stent itself to become blocked with debris, such as fatty deposits. In these circumstances, stents need to be removed and replaced, if possible. In some instances, particularly involving stents made of metal mesh or in the form of a coil, the stent becomes so firmly anchored that it cannot be removed from the vessel or organ. Under such circumstances, surgical procedures may be necessary. The present invention is directed to overcoming the above-mentioned problem with the use of stents in various medical applications.

SUMMARY OF THE INVENTION

The present invention provides an improved stent for use in medical situations which require a device to expand and support a constricted vessel and/or to maintain an open lumen through the vessel of a living being.

In accordance with one aspect of the present invention, a stent is provided which includes one or more members adapted to thrash about within the passage or lumen of the stent to dislodge and break up any debris which may tend to accumulate in the stent so that the debris will move out of the lumen of the stent and prevent blockage of the stent. The movable member (or members) is preferably formed as a flexible wire normally biased to lie in engagement with the stent inner wall to minimize any obstruction in the stent lumen, which wire is responsive to magnetic forces to move about within the stent lumen to dislodge any material tending to accumulate within the stent lumen. The wire member is preferably disposed in a somewhat helical configuration lying against the stent inner wall and is secured at opposite ends to the stent and near opposite ends of the stent itself. The movable member or wire is responsive to magnetic forces, the direction of which may be altered to cause the wire to thrash about within the lumen of the stent.

In accordance with another aspect of the present invention, a method is providing for maintaining the lumen of an implanted stent substantially free of accumulated solids materials wherein magnetic forces are applied from the exterior of the body or organ in which the stent is disposed to cause a member forming part of the stent or disposed within the lumen of the stent to react to such magnetic forces to move about within the stent lumen to dislodge or prevent the accumulation of any solids materials within the stent lumen.

The method contemplates the provision of one or more electromagnets which may be disposed in a predetermined pattern external of the body of the being in which the stent is implanted. The electromagnet or electromagnets may be energized in such a way as to provide magnetic force fields which effect movement of the member within the stent to oscillate or thrash about within the stent lumen to dislodge any accumulated debris or solids materials in the stent lumen.

The improved stent and method in accordance with the invention substantially prolongs the life of a stent implanted within a living being by preventing the accumulation of solids materials within the stent lumen and without requiring invasive procedures to remove such solids materials.

Those skilled in the art will further appreciate the above-mentioned features and advantages of the invention together with other important aspects thereof upon reading the detailed description which follows in conjunction with the drawings.

DETAILED DESCRIPTION OF PREFERRED EMBODIMENTS

Figure 1:
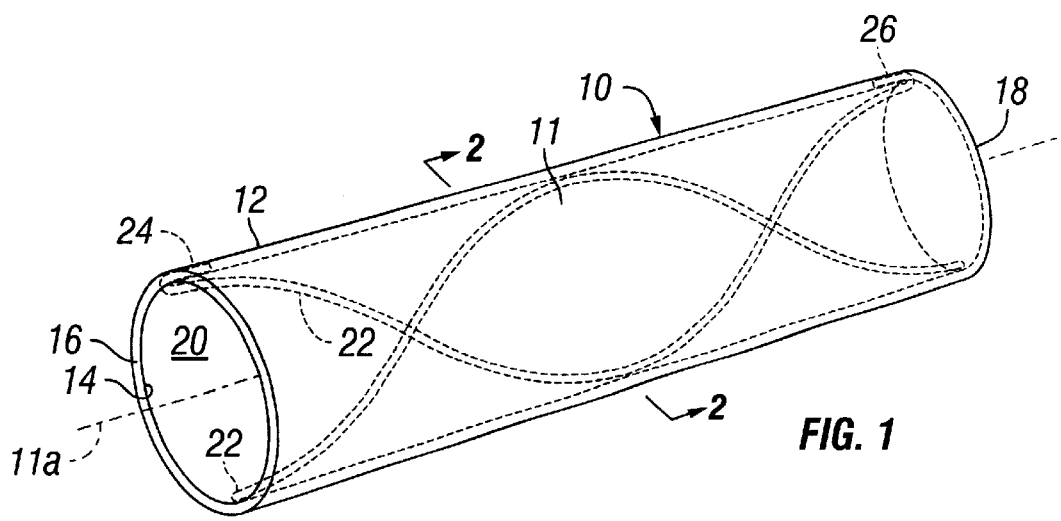
FIG. 1 is a perspective view of one preferred embodiment of an improved stent in accordance with the invention.

In the description which follows, like parts are marked throughout the specification and drawing with the same reference numerals, respectively. The drawing figures are not necessarily to scale and certain features of the invention may be shown in somewhat generalized or schematic form in the interest of clarity and conciseness.

Referring to FIG. 1, there is illustrated a stent in accordance with the present invention for use in medical procedures, which stent is generally designated by the numeral 10. The stent 10 is characterized as an elongated somewhat flexible cylindrical tubular body 11 having a central longitudinal axis 11a, an outer wall surface 12, an inner wall surface 14 and opposed ends 16 and 18. The stent 10 provides an elongated generally cylindrical lumen or passage 20 extending therethrough between the ends 16 and 18.

Figure 2:
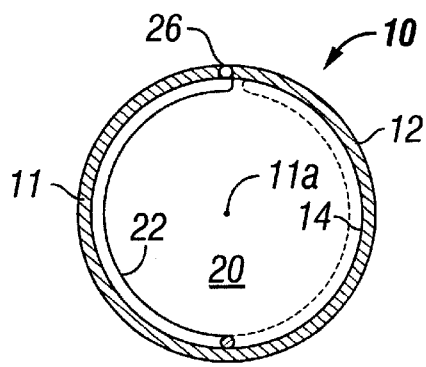
FIG. 2 is a transverse section view taken from line 2—2 of FIG. 1.

The stent 10 is further characterized, as shown in FIGS. 1 and 2, by an elongated flexible member 22 disposed within the interior of the stent and preferably lying against and in engagement with the inner wall 14. The member 22 is preferably characterized as an elongated cylindrical wire formed of a material which is responsive to magnetic forces to move within the lumen 20 substantially laterally. The member 22 may extend in a generally helical path between the stent opposite ends 16 and 18 and may form a substantially complete helical wrap, as shown in FIGS. 1 and 2. Opposite ends of member 22 are designated by numerals 24 and 26. The ends 24 and 26 may be suitably adhered to the stent 10 and fixed so that the member 22 may not move substantially longitudinally within the lumen 20 and is always retained between the ends 16 and 18. The ends 24 and 26 may be hook shaped or provided with a flattened portion embedded within the material of the stent 10 to reliably secure the ends 24 and 26 fixed with respect to the stent. The member 22 is not secured to the stent inner wall surface 14 between the ends 24 and 26 so that, in response to magnetic forces acting thereon, the portion of the member or wire 22 between the ends 24 and 26 may move generally laterally across the lumen 20 and, depending on the changes in the forces acting on the member, may thrash about within the lumen 20 to dislodge any solids materials which may tend to accumulate in and block the cross-sectional area of the lumen 20.

The example of the stent 10 shown in FIGS. 1 and 2 indicates that the wire member 22 makes substantially a complete helical wrap from one end 24 to the opposite end 26, which ends are directly adjacent the opposite ends 16 and 18 of the stent itself. However, the so-called wrap angle of the member 22 may be substantially less than one full 360° wrap. Moreover, it is also considered important that the wire member 22 lie directly against or adjacent to the wall surface 14 so as to not, during normal use of the stent 10, substantially block any portion of the lumen 20. The tubular body 11 of the stent 10 may be formed of one of various materials including plastics or metals of certain types or compositions which have been used previously for stents used in vessels or to minimize lumen closure in living beings. However, if the body 11 of stent 10 is formed of metal, such metal should be nonmagnetic or unresponsive to magnetic forces so as to not alter the effects of magnetic forces acting on the member 22. Although only one wire member 22 may be required for the stent 10, additional wire members may be secured to the stent in the same manner and circumferentially spaced apart around the wall 14. One additional wire member 22 is shown in FIG. 1.

Figure 3:
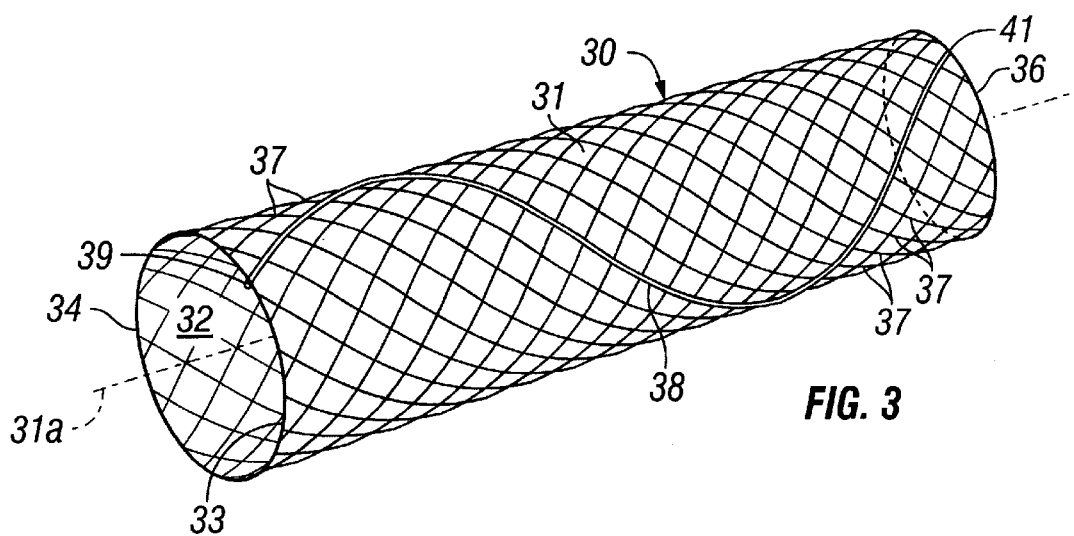
FIG. 3 is a perspective view of an alternate embodiment of a stent in accordance with the invention.

Referring now to FIG. 3, another embodiment of a stent in accordance with the invention, is illustrated and generally designated by the numeral 30. The stent 30 is also formed as an elongated tubular member 31 but is formed of a mesh defining the generally cylindrical tubular body 31. Tubular mesh body 31 includes a longitudinal central axis 31a and defines a through passage or lumen 32 extending between opposed ends 34 and 36. The mesh construction of the stent 30 may comprise plastic or metal threads or wires 37 either woven or fused to each other at their points of intersection. The mesh construction of the stent 30 provides a greater degree of flexibility and collapsibility of the stent in applications where these features are important for placement of the stent. The stent 30 also includes an elongated flexible member comprising a metal wire 38 extending substantially between the ends 34 and 36 and includes opposed ends 39 and 41 which are suitably secured to the tubular body 31 adjacent the body ends 34 and 36. Accordingly, the wire member 38 is not secured to the inner wall surface 33 of the body 31 between its ends and is free, under the influence of magnetic forces, to flex or oscillate laterally within the lumen 32 to dislodge any accumulated solids materials or fatty deposits which might tend to block the lumen 32.

Figure 4:
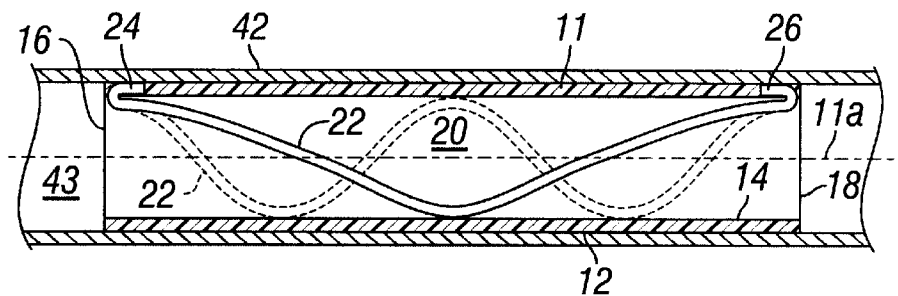
FIG. 4 is a longitudinal central section view of a vessel or duct showing a stent in accordance with the invention disposed therein and illustrating how the passage or lumen clearing member may move about within the lumen of the stent.

FIG. 4 illustrates the stent 10 (alternatively, the stent 30) disposed in a tubular vessel 42 of a living being and having a lumen 43 formed thereby. FIG. 4 also shows an alternate position of the wire member 22 as a consequence of magnetic forces acting thereon to displace the wire member across the lumen 20 substantially throughout the length of the stent 10. The member 22 is preferably provided with an elastic memory so that when the magnetic forces are removed the member returns to the position shown in FIGS. 1 and 2 and by the solid lines of FIG. 4. The member 38 of stent 30 is also, preferably, provided with an elastic memory to bias the member toward inner wall surface 33.

Figure 5:
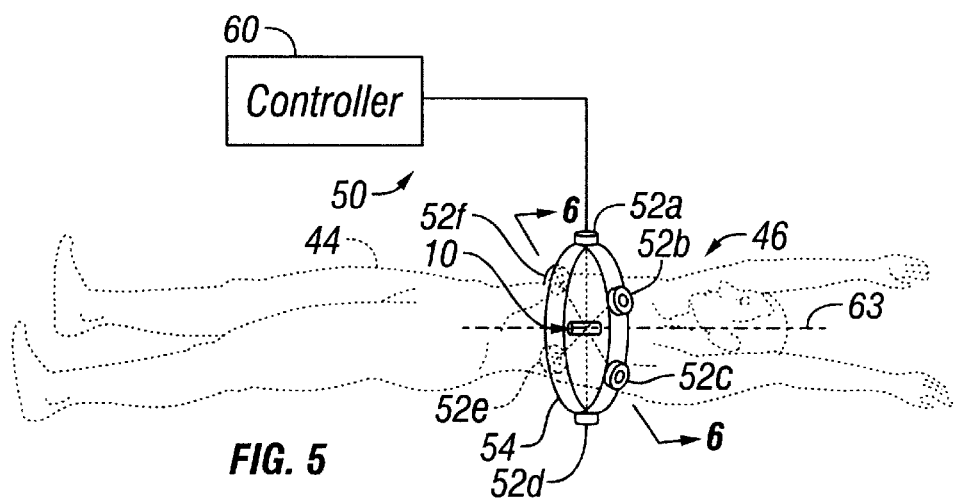
FIG. 5 is a perspective view of a human being including a stent in accordance with the invention implanted therein and illustrating a method of cleaning the stent to be substantially free of accumulation of solids, in accordance with the invention.
Figure 6:
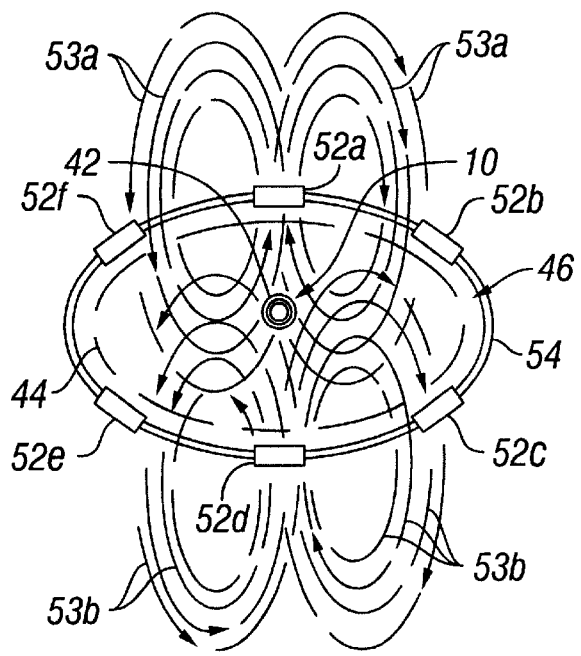
FIG. 6 is a transverse section view taking generally along the line 6–6 of FIG. 5.

Referring now to FIGS. 5 and 6, there is illustrated a system and method for cleaning the lumen 20 of the stent 10, or alternatively, the lumen 32 of the stent 30. The stent 10 is illustrated within the vessel 42 in the body 44 of a human being 46, by way of example. The wire member 22 for the stent 10 is actuated to thrash about within the lumen 20 by an energizing system 50 which includes apparatus comprising a plurality of electromagnets 52a, 52b, 52c, 52d, 52e and 52f, FIG. 6, suitably interconnected by a support strap 54, for example. The electromagnets 52a through 52f are suitably spaced apart such that opposed pairs of magnets 52a and 52d, 52b and 52e and 52c, 52f are generally aligned along common axes, respectively. The electromagnets 52a through 52f are suitably electrically connected to a suitable controller, generally designated by the numeral 60, in such a way that opposed pairs of magnets 52a and 52d, for example, may be energized simultaneously to generate respective magnetic lines of force 53a and 53b, FIG. 6, which pass through the body 44 and exert magnetic forces on the wire member 22 tending to displace the member laterally within the lumen 20. The pairs of electromagnets 52a, 52d and 52b, 52e and 52c, 52f may be sequentially energized so that magnetic forces act on the wire member 22 from different directions rapidly and progressively about the longitudinal central axis of the stent 10. In this way, the member 22 may be caused to thrash about within the lumen 20 to dislodge any accumulated solids materials, such as fatty deposits, which might tend to accumulate within the lumen of the stent. Alternatively, the direction of magnetic forces acting on the member 22 may be reversed by reversing the direction of current flow within the respective pairs of electromagnets previously described. Accordingly, the controller 60 may be adapted to energize opposed pairs of magnets sequentially in one or both directions of sequential energization and the polarity of the electromagnets may be reversed by reversing the direction of current flow therethrough, if desired. Still further, the electromagnets 52a through 52f may not require energization in opposed pairs but each magnet may be energized seriatim in one or more both directions about a central axis 63, for example, see FIG. 5. The number of magnets and pairs of magnets provided in the system 50 may be varied.

The movement of the wire member 22 within the lumen 20 will cause dislodgment of any built-up sediment or fatty deposits thereby keeping the lumen substantially unobstructed. Such treatment will extend the life of a stent such as the stents 10 or 30. Due to the slow accumulation of debris, the procedure would possibly only require to be done infrequently, such as a few times a month. The frequency of the cleaning procedure would depend on the location of the stent, the patient's medications and other clinical factors. Stents in accordance with the invention may be used in major blood vessels, kidney, liver and pancreatic ducts and in narrowed blood vessels elsewhere within the body of a living being. The magnetic forces created by the system 50 are not injurious to living beings but provide a simple external force source for activation of the members 22 or 38.

The construction and use of the stent of the present invention is believed to be understandable to those of ordinary skill in the art based on the foregoing description. Although preferred embodiments of the invention have been described in detail herein, those skilled in the art will further appreciate that various substitutions and modifications may be made to the invention without departing from the scope and spirit of the appended claims.

What is claimed is:

1. A stent including a generally tubular main body having an exterior wall surface and an interior wall surface and opposed ends and defining a lumen extending between said opposed ends, and at least one member disposed within said stent and responsive to magnetic forces acting thereon to move about within said lumen to minimize the accumulation of solids materials therein.

2. The stent set forth in claim 1 wherein:

said member is configured to lie adjacent said inner wall surface.

3. The stent set forth in claim 2 wherein:

said member includes an elastic memory for biasing said member toward said inner wall surface.

4. The stent set forth in claim 1 wherein:

said member comprises an elongated wire extending within said stent and secured at its opposite ends to said tubular body of said stent.

5. The stent set forth in claim 4 wherein:

said wire is formed of a material responsive to magnetic forces acting thereon to be displaced in said lumen.

6. The stent set forth in claim 1 wherein:

said member comprises a flexible metal wire lying adjacent said inner wall surface of said tubular body.

7. The stent set forth in claim 6 wherein:

said member extends in at least a partial helical wrap within said lumen and lying adjacent said inner wall surface.

8. The stent set forth in claim 1 wherein:

said tubular body is formed of a nonmagnetic material.

9. The stent set forth in claim 8 wherein:

said tubular body is formed of a nonmagnetic metal material.

10. The stent set forth in claim 1 wherein:

said tubular body includes a mesh construction of one of metal and nonmetal wire-like components.

11. The stent set forth in claim 1 wherein:

plural members are disposed within said stent and operable to move about in response to magnetic forces acting thereon.

12. A stent for placement in a vessel or duct of a living being, said stent including a generally tubular main body formed of a material unresponsive to magnetic forces, said tubular body including an inner wall surface delimiting an elongated passage or lumen extending between opposite ends of said tubular body; and an elongated flexible member formed of a material responsive to magnetic forces acting on said member to move in one direction or the other, said member being disposed in said lumen of said stent and attached to said stent at spaced apart points thereon whereby in response to magnetic forces acting on said stent, said member will move about within said lumen to minimize the accumulation of solids materials therein.

13. The stent set forth in claim 12 wherein:

said member comprises an elongated wire having an elastic memory for biasing said wire toward said inner wall surface.

14. A method for providing a passageway in a vessel within a living being comprising the steps of:

placing a stent within said vessel including a member disposed within a lumen of said stent which is responsive to magnetic forces acting thereon to move about within said lumen of said stent to minimize the accumulation of solids materials in said lumen of said stent;

generating magnetic forces in the vicinity of said stent sufficient to cause said member to move about within said lumen of said stent to minimize the accumulation of said solids materials therein.

15. The method set forth in claim 14 including the step of:

causing said magnetic forces to fluctuate in intensity.

16. The method set forth in claim 14 including the step of:

causing said magnetic forces to change direction.

17. The method set forth in claim 14 including the step of:

placing a system in the vicinity of said vessel comprising a plurality of electromagnets and energizing said electromagnets in a predetermined manner to generate a fluctuating magnetic force field in the vicinity of said stent.

18. The method set forth in claim 17 including the steps of:

providing said system with plural electromagnets arranged in opposed pairs and energizing selected pairs of said electromagnets in a predetermined sequence to change the direction of magnetic forces acting on said member of said stent to effect movement thereof within said lumen of said stent.

19. A method for maintaining a passageway in a vessel within a living being to allow substantially unobstructed fluid flow therethrough wherein said vessel includes a stent disposed therein, said stent including a lumen and a member responsive to magnetic forces acting thereon to move about within said lumen of said stent, said method including the steps of:

placing an apparatus in the vicinity of said vessel including means for generating magnetic forces sufficient to act on said member to cause said member to move about within said lumen of said stent to minimize the accumulation of solids materials in said lumen of said stent.

20. The method set forth in claim 19 including the steps of:

providing said apparatus with plural electromagnets arranged in a selected pattern; and energizing said electromagnets to generate sufficient magnetic forces acting on said member to move said member within said lumen of said stent.

* * * * *